United States Patent [19]
Bennion et al.

[11] Patent Number: 4,748,160
[45] Date of Patent: May 31, 1988

[54] ANGIOTENSIN CONVERTING ENZYME INHIBITORS AND THEIR FORMULATION AND USE AS PHARMACEUTICALS

[75] Inventors: Colin Bennion, Loughborough; David P. Marriott, Radcliffe-on-Trent; Anthony R. Cook, Nottingham; David H. Robinson, Shepshed, all of United Kingdom

[73] Assignee: Fisons plc, Ipswich, England

[21] Appl. No.: 797,934

[22] Filed: Nov. 14, 1985

[30] Foreign Application Priority Data

Nov. 30, 1984 [GB] United Kingdom ................. 8430295
Mar. 6, 1985 [GB] United Kingdom ................. 8505798
May 21, 1985 [GB] United Kingdom ................. 8512875

[51] Int. Cl.⁴ ..................... A61K 31/55; C07D 285/36

[52] U.S. Cl. ...................... 514/82; 514/482; 514/114; 514/86; 514/89; 514/94; 514/92; 514/95; 514/96; 514/99; 514/100; 514/211; 514/259; 514/256; 514/311; 514/357; 514/365; 514/367; 514/374; 514/375; 514/394; 514/399; 514/443; 514/438; 514/469; 514/471; 544/283; 544/335; 546/125; 546/332; 562/439; 562/426; 562/507; 562/560; 558/154; 540/489; 549/58; 549/76; 549/77; 548/467; 548/491; 548/495; 548/561; 548/305; 548/341; 548/217; 548/236; 548/180; 548/204

[58] Field of Search ............... 562/439, 426, 507, 560; 558/154; 540/489; 549/58, 76, 77; 548/467, 491, 495, 561, 305, 341, 217, 236, 180, 204; 544/283, 335; 546/125, 332; 514/114, 82, 86, 89, 94, 92, 95, 96, 99, 100, 211, 254, 256, 311, 357, 365, 367, 374, 375, 394, 399, 443, 438

[56] References Cited

U.S. PATENT DOCUMENTS 2,514,219 7/1950 Shotton ............................... 540/489

Primary Examiner—Robert T. Bond
Attorney, Agent, or Firm—Marshall, O'Toole, Gerstein, Murray & Bicknell

[57] ABSTRACT

There are described compounds of formula I, $$ZCHRCON(-N=CR_4R_5)CHR_6(CH_2)_nCOY \qquad I$$

where the substituents are defined in the disclosure.

There are also described methods for making the compounds, formulations containing them and their use, e.g. as antihypertensives.

11 Claims, No Drawings

ANGIOTENSIN CONVERTING ENZYME INHIBITORS AND THEIR FORMULATION AND USE AS PHARMACEUTICALS

This invention relates to new compounds, methods for their preparation and compositions containing them.

A wide variety of angiotensin converting enzyme (ACE) inhibitors are known, e.g. from European Patent Specifications Nos. 0112511 and 121830.

We have now found a group of compounds having advantageous properties, e.g. as ACE inhibitors.

According to the invention we provide compounds of formula I, $$ZCHRCON(-N=CR_4R_5)CHR_6(CH_2)_nCOY \qquad I$$

in which

Z is $R_2CH(COOH)NH-$, $R_1SCH_2-$ or $Ph(CH_2)_pPO(OH)-$,

Ph is phenyl, p is an integer from 1 to 6, $R_1$ is hydrogen or $R_8CO-$, $R_8$ is alkyl C1 to 10 or phenyl, R is hydrogen or alkyl C1 to 10, $R_2$ is alkyl C1 to 10 or phenylalkyl C7 to 12, $R_4$ and $R_5$, which may be the same or different, are each hydrogen, phenyl, naphthyl; a 5 or 6 membered alicyclic or heterocyclic ring each of which is optionally fused to a benzene ring; cycloalkyl containing 3 to 7 carbon atoms; or alkyl C1 to 10 optionally substituted by phenyl, naphthyl or a 5 or 6 membered heterocyclic ring which latter is optionally fused to a benzene ring, the phenyl, naphthyl or 5 or 6 membered alicyclic or heterocyclic ring (which latter two are optionally fused to a benzene ring) are all optionally substituted by one or more alkyl C1 to 10, alkoxy C1 to 10, halogen, phenylalkyl C7 to 12, phenylalkoxy C7 to 12, phenyl, hydroxy, =O, fluoroalkyl C1 to 10, cyano, nitro, phenylsulphonamido, dialkyl (C1 to 10)-amino-alkoxy (C1 to 10), alkylthio C1 to 10, or dialkyl (C1 to 10)-amino, or $R_4$ and $R_5$ together form a $-(CH_2)_4-$, $-(CH_2)_5-$,

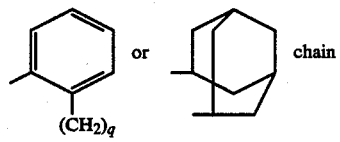

$R_6$ is hydrogen or alkyl C1 to 10, q is 2 or 3, n is 0 or 1,

Y is hydroxy or $-NHSO_2R_9$, and $R_9$ is alkyl C1 to 10, and pharmaceutically acceptable salts, esters and amides thereof.

According to the invention we also provide a process for the production of a compound of formula I, or a pharmaceutically acceptable salt, ester or amide thereof, which comprises (a) removal of a protecting group from a compound of formula I in which one or more of the amino or carboxylic acid groups is protected, (b) reaction of a protected derivative of a compound of formula II, $$ZCHRCOX \qquad II$$

in which Z and R are as defined above, and X is a good leaving group, with a compound of formula III, $$HN(-N=CR_4R_5)CHR_6(CH_2)_nCOY \qquad III$$

or a salt, ester or protected derivative thereof, in which $R_4$, $R_5$, $R_6$, n and Y are as defined above, (c) production of a compound of formula I in which $R_1$ is hydrogen by selective cleavage of a corresponding compound of formula I in which $R_1$ is $R_8CO-$, or (d) reaction of a compound of formula VII, $$ZCHRCON(NH_2)CHR_6(CH_2)_nCOY \qquad VII$$

in which Z, R, $R_6$, n and Y are as defined above, with a compound of formula VIII, $$R_4COR_5 \qquad VIII$$

in which $R_4$ and $R_5$ are as defined above, and where desired or necessary deprotecting the resulting compound, or converting a compound of formula I to a pharmaceutically acceptable salt, ester or amide thereof or vice versa.

In process (a) the protecting group can be any convenient protecting group conventionally used in peptide synthesis and may be removed using techniques conventionally used in peptide synthesis. Thus carboxy protecting groups which may be used are alkoxy, e.g. C1 to 6 alkoxy such as t-butyloxy, or benzyloxy groups which can be removed, for example by hydrolysis, e.g. basic hydrolysis using aqueous methanolic sodium hydroxide; or cleavage using, for example, trifluoroacetic acid; or by hydrogenation. Amino-protecting groups which may be mentioned include benzyloxycarbonyl or t-butyloxycarbonyl. We prefer to use starting materials in which the carboxy groups are protected.

In process (b) the group X may be, for example, halo, e.g. bromo or chloro. The reaction may be carried out at a temperature of from 0° to 50° C. The reaction may conveniently be carried out in a non-nucleophilic solvent under basic conditions, e.g. in toluene with polyvinylpyridine.

In process (c) the reaction is conveniently carried out in a solvent which is inert under the reaction conditions, e.g. methanol. The reaction is preferably carried out under basic conditions, e.g. in the presence of ammonia or potassium hydroxide.

Process (d) may be carried out in the presence of an acid catalyst, e.g. aqueous hydrochloric acid, and in the presence of a protic solvent, e.g. ethanol. The reaction may be carried out at an elevated temperature, e.g. 50° to 80° C.

The starting materials for the above processes are either known or may be made from known compounds using conventional processes. Thus compounds of formulae IV and V, $$H_2N-NHCHR_6(CH_2)_nCOY \qquad IV$$

$$R_4COR_5 \qquad V$$

may be reacted to yield a compound of formula III, e.g. in a lower alkanol such as ethanol, at a temperature of from about 0° to 90° C.

The compounds of formula IV may be made by reacting hydrazine with a compound of formula VI, $$XCHR_6(CH_2)_nCOY \quad VI$$

In the above reaction scheme $R_4$, $R_5$, $R_6$, X, n and Y have the significances given earlier and the reactions may be carried out using conventional reaction conditions.

Compounds of formula VII may be made by processes analogous to process (b) above.

The compounds of formula I, and the intermediates therefor, may be isolated from their reaction mixtures using conventional techniques known per se.

The processes described above may produce the compound of formula I or a derivative thereof. It is also within the scope of this invention to treat any derivative so produced to liberate the free compound of formula I, or to convert one derivative into another.

In addition to the processes described above the compounds of formula I may be made by a variety of processes which are analogous to those known for the production of structurally similar compounds.

Pharmaceutically acceptable salts of the compounds of formula I include ammonium salts, alkali metal salts, e.g. sodium and potassium salts (which are preferred); alkaline earth metal salts, e.g. the calcium and magnesium salts; salts with organic bases, e.g. salts with dicyclohexylamine or N-methyl-D-glucamine; and salts with amino acids, e.g. with arginine, lysine etc. Also, when Z is $R_2CH(COOH)NH$—, salts with organic or inorganic acids may be prepared, e.g. with HCl, HBr, $H_2SO_4$, $H_3PO_4$, methanesulfonic, toluensulfonic, maleic, fumaric or camphorsulfonic acids. The non-toxic physiologically acceptable salts are preferred, eg the sodium salts are preferred for water solubility, although other salts are also useful, e.g. in isolating or purifying the product. Pharmaceutically acceptable esters include alkyl C1 to 6, e.g. ethyl, esters and esters with benzyl alcohol. We specifically provide compounds in which Z is $R_2CH(COOH)NH$— and the two —COOH groups (i.e. where Y is —OH) are in different forms, e.g. where one is esterified and the other is not. More specifically we provide such compounds in which the —COOH group adjacent to the $R_2$ group is esterified.

The salts may be formed by conventional means, e.g. by reacting the free acid or free base forms of the product with one or more equivalents of the appropriate base or acid in a solvent or medium in which the salt is insoluble, or in a solvent such as water which is then removed in vacuo, or by freeze-drying, or by exchanging the ions of an existing salt for another ion on a suitable ion exchange resin. The esters may be made by using the appropriate starting materials in the reaction sequence given above or by esterification of the free acid.

When Z is $R_2CH(COOH)NH$— we prefer the partial structure —NHCHRCO— in formula I to be part of a naturally occurring amino acid. Where any alkyl, alkoxy or substituted alkyl groups are present they may individually be straight or branched and contain up to and including 6 carbon atoms.

Where any halogen atoms are present they may be bromine, fluorine or preferably chlorine atoms. A specific fluoroalkyl group which may be mentioned is —$CF_3$. As a dialkylaminoalkoxy group we prefer diethylaminoethoxy and as a specific alkylthio group there may be mentioned methylthio. Five or 6 membered heterocyclic groups which are provided include thiophenyl, furyl, pyrrolyl, imidazolyl, oxazolyl, thiazolyl, pyrimidinyl or pyridyl, each of which may be fused to a benzene ring.

We prefer R to be hydrogen or alkyl C1 to 6, e.g. methyl. We also prefer $R_2$ to be benzyl or more preferably phenylethyl.

We prefer $R_6$ to be methyl or more preferably hydrogen and n to be 0. $R_1$ preferably hydrogen, benzoyl or alkanoyl C2 to 6, e.g. acetyl or pivaloyl. We also prefer Y to be —OH, or a salt or alkyl C1 to 6 ester thereof.

We prefer one of $R_4$ and $R_5$ to be methyl, phenyl or more preferably hydrogen. The other of $R_4$ and $R_5$ may be 1- or 2-naphthyl, cyclohexyl, alkyl C1 to 4 (preferably branched), pyridyl (e.g. 2- or 3-pyridyl), thienyl (e.g. 2-thienyl), thiazolyl (e.g. thiazol-2-yl) which may be substituted by alkyl C1 to 6 (e.g. methyl); or phenyl optionally substituted by one or two chlorine atoms, by —CN, by phenylsulphonylamino, by another phenyl, by alkoxy C1 to 6 (e.g. methoxy), by alkyl C1 to 6 (e.g. butyl), or by hydroxy.

Alternatively $R_4$ and $R_5$ may together form a dihydronaphthylidene, a cyclohexylidene, an adamantylidene or an optionally oxo substituted dihydroindolyl group.

We prefer $R_4$ and $R_5$ not to include an aryl ring in which the aryl ring contains two or three substituents other than hydrogen.

We particularly prefer those compounds in which $R_2$ is phenylethyl, R is methyl, $R_4$ and $R_6$ are both hydrogen, $R_5$ is phenyl, or alkyl or cycloalkyl containing up to 6 carbon atoms, eg cyclohexyl, n is 0 and Y is —OH. A further preferred group of compounds are those in which $R_1$ is hydrogen or $R_8$ is phenyl, R is methyl, $R_4$ is hydrogen, $R_5$ is alkyl or cycloalkyl containing up to 6 carbon atoms, eg cyclohexyl, n is 0 and Y is —OH.

Specific groups of compounds of formula I which may be mentioned are:

(a) those in which neither of $R_4$ and $R_5$, when they represent phenyl, naphthyl or a 5 or 6 membered alicyclic or heterocyclic ring can be substituted by hydroxy or =O, and (b) those in which $R_4$ and $R_5$, which may be the same or different, are each hydrogen, alkyl C1 to 6, phenyl, naphthyl or a 5 or 6 membered heterocyclic ring, the phenyl optionally being substituted by one or more alkyl C1 to 6, alkoxy C1 to 6 or halogen groups, or $R_4$ and $R_5$ together form a —$(CH_2)_4$— or —$(CH_2)_5$— or

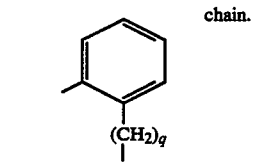

chain.

The compounds of formula I may contain one or more asymmetric carbon atoms and may therefore exhibit optical and/or diastereo isomerism. Diastereoisomers may be separated using conventional techniques, e.g. chromatography or fractional crystallisation. The various optical isomers may be made by separation of a racemic or other mixture of the compounds using conventional, eg. fractional crystallisation or HPLC, techniques. Alternatively the desired optical isomers may be made by reaction of the appropriate optically active starting materials under conditions which will not cause racemisation. We prefer those compounds of formula I in which any asymmetric carbon atoms are in the S configuration.

The compounds of the invention are advantageous in that they are more efficaceous, produce less side effects, are longer acting, more readily absorbed, less toxic, distributed in the body tissues in a different manner or have other advantageous properties when compared to compounds of similar structure.

The compounds of the invention are useful because they possess pharmacological properties. In particular they inhibit angiotensin converting enzyme and thus block conversion of the decapeptide angiotensin I to angiotensin II (see Example A). Angiotensin II is a potent vasoconstrictor in mammals. It also stimulates aldosterone release which results in salt and fluid retention. Increased blood pressure is the physiological result of these changes. Inhibitors of angiotensin converting enzyme are thus effective antihypertensive agents in a variety of animal models (see Example B) and are indicated for use clinically, for example, in patients with renovascular, malignant or essential hypertension or chronic congestive heart failure. See, for example, D W Cushman et al., *Biochemistry* 16, 5484 (1977) and E W Petrillo and M A Ondetti, Med. Res. Rev. 2 93 (1982).

Thus, the compounds of this invention are useful as antihypertensives in treating hypertensive mammals, including humans and they can be utilised to achieve reduction of blood pressure, e.g. in formulations containing appropriate pharmaceutically acceptable excipients, diluents or carriers. The compounds of the invention can be administered (to animals or humans) in unit dosages of 5 to 500 mg generally given several times, e.g. 1 to 4 times, per day thus giving a total daily dose of from 5 to 2000 mg per day. The dose will vary depending on the type and severity of disease, weight of patient and other factors which a person skilled in the art will recognise.

The compounds of this invention may be given in combination with other pharmaceutically active compounds, e.g. diuretics or antihypertensives. The dosage of the other pharmaceutically active compound can be that conventionally used when the compound is administered on its own, but is preferably somewhat lower. To illustrate these combinations, one of the antihypertensives of this invention effective clinically in the range, e.g. 15–200 milligrams per day, can be combined at levels ranging, e.g. from 3–200 milligrams per day with the following antihypertensives and diuretics in dose ranges per day as indicated:

hydrochlorothiazide (15–200 mg), chlorothiazide (125–2000 mg), ethacrynic acid (15–200 mg), amiloride (5–20 mg), furosemide (5–80 mg), propanolol (20–480 mg), timolol (5–50 mg) nifedipine (20–100 mg), verapamil (120–480 mg) and methyldopa (65–2000 mg). In addition, the triple drug combinations of hydrochlorothiazide (15–200 mg) plus amiloride (5–20 mg) plus converting enzyme inhibitor of this invention (3–200 mg) or hydrochlorothiazide (15–200 mg) plug timolol (5–50 mg), plus the converting enzyme inhibitor of this invention (3–200 mg) are contemplated. The above dose ranges may be adjusted on a unit basis as necessary to permit divided daily dosage. Also, the dose may vary depending on the severity of the disease, weight of patient and other factors which a person skilled in the art will recognise.

According to our invention we also provide a pharmaceutical composition comprising preferably less than 80%, more preferably less than 50%, e.g. 1 to 20%, by weight of a compound of formula I, or a pharmaceutically acceptable salt or ester thereof, in admixture with a pharmaceutically acceptable adjuvant, diluent or carrier.

Thus the compound may be put up as a tablet, capsule, dragee, suppository, suspension, solution, injection, implant, a topical, e.g. transdermal, preparation such as a gel, cream, ointment, aerosol or a polymer system, or an inhalation form, e.g. an aerosol or a powder formulation.

We prefer compositions which are designed to be taken oesophageally and to release their contents in the gastrointestinal tract. Thus we prefer tablets which may, for example, be made by direct compression. In such a process the active ingredient is mixed with one or more of modified forms of starch, calcium phosphate, a sugar e.g. lactose, microcrystalline cellulose and/or other directly compressible excipients, together with lubricant(s), e.g. stearic acid or magnesium stearate, flow aid(s), e.g. talc or colloidal silicon dioxide, and disintegrant(s), e.g. starch or the materials sold under the Trade Marks, Nymcel, Ac-Di-Sol, Explotab and Plasdone XL. Tablets are then formed by direct compression, and may be sugar or film coated e.g. with hydroxypropylmethylcellulose.

Alternatively the active ingredient may be granulated before tabletting. In such cases the active ingredient is mixed with one or more of starch, calcium phosphate, a sugar e.g. lactose, microcrystalline cellulose or other suitable excipients and granulated with a binder such as starch, pregelled starch, polyvinylpyrrolidone, gelatine, a modified gelatine, or a cellulose derivative, e.g. hydroxypropylmethylcellulose. The mass is then dried, sieved and mixed with lubricant(s), flow aid(s) and disintegrant(s), such as described in the previous paragraph. Tablets are then formed by compression of the granules, and may be sugar or film coated, e.g. with hydroxypropylmethylcellulose.

As a further alternative a powder, blend or granules, such as are described above as intermediates in tabletting, may be filled into a suitable, e.g. gelatine, capsule.

In order to improve the bioavailability, or decrease variability of availability, of the active ingredient the compound may be:

(a) dissolved in a suitable solvent, e.g. polyethylene glycol, Gelucaire, arachis oil, a (hydrogenated) vegetable oil or beeswax and the solution is then filled into a gelatine capsule, (b) produced as a spray-dried or freeze-dried form prior to mixing with other excipients, (c) milled and/or micronised to produce a powder with a large surface area prior to mixing with other excipients, (d) made into a solution and distributed over an inert excipient having a large surface area, e.g. colloidal silicon dioxide. The solvent is evaporated and further excipients added, (e) formed into a complex with cyclodextrin prior to mixing with other excipients. This complex also assists in increasing light stability, or (f) made into a solid solution or co-precipitated, e.g. with polyvinylpyrrolidone, polyethyleneglycol, modified cellulose, hydroxypropylmethylcellulose, urea or a sugar prior to mixing with further excipients.

The compounds, either in their normal form or in a modified form, e.g. as described immediately above, may be formulated in a controlled release form. Thus the compound may be dispersed, or contained in, a polymer matrix formed from, for example, ethylcellulose, hydroxypropylmethylcellulose or the product sold under the Trade Mark Eudragit. Alternatively the compound may be formulated as a tablet or beads which are surrounded by a semi-permeable membrane, e.g. shellac, ethylcellulose or an acrylate/methacrylate polymer.

Certain of the compounds of formula I can form hydrates or solvates, e.g. with an alcohol such as ethanol or with diethyl ether or toluene.

Certain of the compounds of formula I, i.e. those in which Z is a group $HSCH_2-$, may exist in a tautomeric cyclised form of formula Ia,

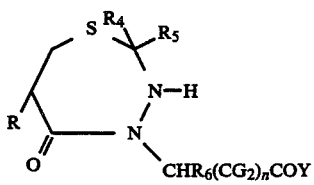

in which R, $R_4$, $R_5$, $R_6$, n and Y are as defined above.

Appropriate compounds of formula I and Ia may exist in equilibrium in solution.

We have in particular found that compounds of formula Ia are a favoured solid form of the compounds when $R_4$ is alkyl and $R_5$ is hydrogen,, or when $R_4$ is phenyl, $R_5$ is hydrogen and $R_6$ is alkyl.

Compounds of formula Ia are included within the scope of the present invention.

The invention is illustrated, but in no way limited by the following Examples.

EXAMPLE 1

(S)-1-(3-Mercapto-2-methyl-1-oxopropyl)-2-(phenylmethylene)-1-hydrazinoacetic acid (a) Ethyl 2-phenylmethylene-1-hydrazinoacetate A mixture of ethyl hydrazinoacetate hydrochloride (1.55 g), benzaldehyde (1.0 ml) and triethylamine (1.0 ml) in ethanol (20 ml) was heated at reflux for 0.5 hour. The cooled solution was treated with ether to produce a white precipitate. The solid was removed by filtration and the filtrate evaporated to a colourless oil. Purification by chromatography yielded the sub-title product (1.55 g) as a gum.

(b) Ethyl (S)-1-(3-acetylthio-2-methyl-1-oxopropyl)-2-(phenylmethylene)hydrazinoacetate A solution of the product of step (a) (1.0 g) in toluene (10 ml) was treated with polyvinylpyridine (1.0 g) and 3-(acetylthio)-2-methyl propanoyl chloride and the reaction mixture stirred at room temperature for 3 hours. The solids were removed by filtration and the filtrate evaporated to a gum. A solution of the residue in ether was washed with sodium bicarbonate solution, water and dried (anh $Na_2SO_4$). Evaporation gave an oil. Purification of the residue by chromatography gave the sub-title product (1.5 g) as a clear gum.

Mass spectrum showed M+ 350.
$C_{17}H_{22}N_2O_4S$ MW 350.

(c) (S)-1-(3-Mercapto-2-methyl-1-oxopropyl)-2-(phenylmethylene)hydrazinoacetic acid dicyclohexylamine salt A solution of potassium hydroxide (0.48 g) in water (10 ml) was added to a solution of the product of step (b) in methanol and the reaction mixture stirred for 20 hours at room temperature. The solution was acidified with dilute hydrochloric acid, extracted with ethyl acetate and the extract washed with water, dried and evaporated to yield the free acid as an oil. A solution of the residue in ether was treated with dicyclohexylamine to yield the product salt (0.6 g) as a white solid (mp 173°-6°).

$C_{13}H_{16}N_2O_3S.C_{12}H_{23}N$ Requires: C 65.04, H 8.51, N 9.10, S 6.95%. Found: C 65.19, H 8.23, N 8.99, S 6.77%.

Mass spectrum showed M+ 280.
$C_{13}H_{16}N_2O_3S$ MW 280.

EXAMPLE 2

The following compounds were made by the process of Example 1.

(a) (S)-1-(3-Mercapto-2-methyl-1-oxopropyl)-2-(1-naphthylmethylene)-1-hydrazinoacetic acid M.p. 119°-20°.
$C_{17}H_{18}N_2O_3S$ Requires: C61.62, H5.45, N8.48, S9.70%. Found: C61.81, H5.66, N8.34, S9.81%.

(b) (S)-1-(3-Mercapto-2-methyl-1-oxopropyl)-2-(2-naphthylmethylene)-1-hydrazinoacetic acid dicylcohexylamine salt M.p. 174°-177°.
$C_{29}H_{41}N_3O_3S$ Requires: C68.10, H8.02, N8.22, S6.26%. Found: C68.42, H8.10, N8.21, S6.21%.

(c) (S)-1-(3-Mercapto-2-methyl-1-oxopropyl)-2-(3,4-dihydronaphthylidene)-1-hydrazinoacetic acid M.p. 147°-50°.
$C_{16}H_{20}N_2O_3S$ Requires: C60.00, H6.25, N8.75, S10.00%. Found: C60.12, H6.13, N8.82, S10.26%.

(d) 2-[(2,6-Dichlorophenyl)methylene]-1-(3-mercapto-1-oxopropyl)-1-hydrazinoacetic acid M.p. 142°-143°.
$C_{12}H_{12}Cl_2N_2O_3S$ Requires: C43.00, H3.61, N8.36, S9.56, Cl21.15%. Found: C43.17, H3.58, N8.17, S9.69, Cl20.83%.

(e) (S)-1-(3-Mercapto-2-methyl-1-oxopropyl)-2-(1-phenylethylidene)-1-hydrazinoacetic acid dicyclohexylamine salt M.p. 155°-8°.
$C_{14}H_{18}N_2O_3S.C_{12}H_{23}N$ Requires: C65.68, H8.63, N8.84, S6.74%. Found: C65.29, H8.31, N8.64, S6.80%.

(f) (S)-1-(3-Mercapto-2-methyl-1-oxopropyl)-2-(diphenylmethylidine)-1-hydrazinoacetic acid dicyclohexylamine salt M.p. 148°-150°.
$C_{19}H_{20}N_2O_3S.C_{12}H_{23}N$ Requires: C69.27, H8.00, N7.82%. Found: C69.26, H7.84, N8.04%.

(g)
(S)-2-[(4-Cyanophenyl)methylene]-1-(3-mercapto-2-methyl-1-oxopropyl)-1-hydrazinoacetic acid M.p. 168°-70°.

$C_{14}H_{15}N_3O_3S$ Requires: C55.08, H4.92, N13.77, S10.49%. Found: C54.86, H4.94, N13.54, S10.48%.

(h)
(S)-2-[((4-Phenylsulphonamido)phenyl)methylene]-1-(3-mercapto-2-methyl-1-oxopropyl)-1-hydrazinoacetic acid dicyclohexylamine salt, diethyl etherate M.p. Decomposes rapidly.

$C_{19}H_{21}N_3O_5S_2 \cdot C_{12}H_{23}N \cdot C_4H_{10}O$ Requires: C60.76, H7.68, N8.33, S9.52%. Found: C60.52, H7.62, N8.24, S9.32%.

(i)
(S)-2-Cyclohexylmethylene-1-(3-mercapto-2-methyl-1-oxopropyl)-1-hydrazinoacetic acid and 2-Cyclohexylhexahydro-6-(S)-methyl-5-oxo-[1,3,4-thiadiazepinyl]-4-acetic acid M.p. 87°-90°.

$C_{13}H_{22}N_2O_3S$ Requires: C54.55, H7.69, N9.79, S11.19%. Found: C54.13, H7.25, N9.74, S11.39%.

Evidence for the presence of the cyclic species comes from n.m.r. spectroscopy. A spectrum (360 MH$_2$) of the solid in deuterochloroform at time=10 minutes indicates the presence of cyclic species only. This changes over several hours to an equilibrium mixture of the cyclic and acyclic forms.

(j)
(S)-1-(3-Mercapto-2-methyl-1-oxopropyl)-2-(2-methyl propylidene)-1-hydrazinoacetic acid dicyclohexylamine salt and Hexahydro-6-methyl-2-(1-methyl-ethyl)-5-oxo-[1,3,4-thiadiazepinyl]-4-acetic acid dicyclo hexylamine salt M.p. 134°-7°.

$C_{10}H_{18}N_2O_3S \cdot C_{12}H_{23}N$ Requires: C61.83, H9.60, N9.84, S7.49%. Found: C61.41, H9.21, N9.75, S7.48%.

(k)
(S)-2-Adamantylidene-1-(3-mercapto-2-methyl-1-oxo propyl)-1-hydrazinoacetic acid and Hexahydro-6-(S)-methyl-5-oxo-spiro[1,3,4-thiadiazepine-2,2'-tricyclo[3,3,1,1$^{3,7}$]decane]-4-acetic acid M.p. 190°-1°.

$C_{16}H_{24}N_2O_3S$ Requires: C59.23, H7.46, N8.63, S9.88%. Found: C59.56, H7.23, N8.50, S9.72%.

(l)
(S)-2-Adamantylidene-1-(3-mercapto-2-methyl-1-oxopropyl)-1-hydrazinoacetic acid sodium salt and Hexahydro-6-(S)-methyl-5-oxo-spiro[1,3,4-thiadiazepine-2,2'-tricyclo-[3,3,1,1$^{3,7}$]decane]-4-acetic acid sodium salt Formed by treating an aqueous solution of the product of Example 2(k) (either form) with one equivalent of sodium bicarbonate and freeze drying.

$C_{16}H_{23}N_2NaO_3S$ 1.5H$_2$O Requires: C51.44, H7.02, N7.53, S8.58. Found: C51.05, H6.16, N7.55, S8.66.

A mass spectrum (Fast Atom Bombardment) shows peaks at 325 (M+H)$^+$ and 347 (M+Na+H)$^+$ (m)
(S)-2-[(1,1'-Biphenyl)-4-ylmethylene]-1-(3-mercapto-2-methyl-1-oxopropyl)-1-hydrazinoacetic acid M.p. 169°-171°.

$C_{19}H_{20}N_2O_3S$ Requires: C64.04, H5.62, N7.86, S8.99%. Found: C63.90, H5.39, N7.87, S8.87%.

(n)
(S)-2-Cyclohexylidene-1-(3-mercapto-2-methyl-1-oxopropyl)-1-hydrazinoacetic acid The product retained a trace of toluene of crystallisation.

M.p. 122°-125°.

$C_{12}H_{20}N_2O_3S$, 0.2 C$_7$H$_8$ Requires: C55.24, H7.48, N9.68, S11.06%. Found: C55.21, H7.50, N9.62, S11.28%.

(o)
(S)-1-(3-Mercapto-2-methyl-1-oxopropyl)-2-(2,2-dimethylpropylidene)-1-hydroazinoacetic acid M.p. 96°-8°.

$C_{11}H_{20}N_2O_3S$ Requires: C50.77, H7.69, N10.77, S12.31%. Found: C51.00, H7.63, N10.78, S12.24%.

EXAMPLE 3

(S)-2-(4-Chlorophenylmethylene)-1-(3-mercapto-2-methyl-1-oxopropyl)-1-hydrazinoacetic acid (a) Ethyl (S)-1-(3-acetylthio-2-methyl-1-oxopropyl-1-hydrazinoacetate Ethyl hydrazinoacetate hyrochloride (15.5 g) and triethylamine (28.0 ml) were stirred in acetone (400 ml) for 0.5 hour. The mixture was cooled to below 10°, a solution of 3-(acetylthio)-2-methyl propanoyl chloride (18.05 g) in acetone (100 ml) added dropwise over 0.5 hour and the reaction mixture stirred at room temperature for a further 16 hours. The solids were removed by filtration and the filtrate evaporated to dryness. The residual gum was dissolved in 50% aqueous acetic acid, evaporated to dryness and azeotroped with toluene leaving an oily residue. Purification by HPLC gave the sub-title product (19.5 g) as a gum.

Mass spectrum showed M+262.

$C_{10}H_{18}N_2O_4S$ MW 262.

(b) Ethyl (S)-1-(3-acetylthio-2-methyl-1-oxopropyl)-2-(4-chlorophenylmethylene)-1-hydrazinoacetate The product from step (a) (1.05 g), 4-chlorobenzaldehyde (0.56 g) and dilute hydrochloric acid (1 drop) were refluxed in ethanol (20 ml) for two hours. The solution was evaporated to an oil. Purification by chromatography gave the sub-title product (1.0 g) as a clear gum.

Mass spectrum showed M+ 384/6.

$C_{17}H_{21}ClN_2O_4S$ MW 384/5.

(S)-2-(4-Chlorophenylmethylene)-1-(3-mercapto-2-methyl-1-oxopropyl)-1-hydrazinoacetic acid A solution of potassium hydroxide (0.46 g) in water (10 ml) was added to a solution of the product of step (b) (0.9 g) in methanol (5 ml) and the reaction mixture stirred for 20 hours at room temperature under a nitrogen atmosphere. The solution was acidified with dilute hydrochloric acid and extracted with ethyl acetate. The extracts were washed with water, dried and evaporated to a gum. Purification by chromatography gave the title product (0.35 g) as a white solid, mp 135°–7°.

$C_{13}H_{15}ClN_2O_3S$ Requires: C49.60, H4.80, N8.90, Cl 11.26, S10.19%. Found: C49.80, H4.79, N8.83, Cl 11.47, S10.52%.

Mass spectrum showed M+314/6.
$C_{13}H_{15}ClN_2O_3S$ MW 314/5.

EXAMPLE 4

The following compounds were made by the process of Example 3.

(a)
(S)-2-[(2,6-Dichlorophenyl)methylene]-1-(3-mercapto-2-methyl-1-oxopropyl)-1-hydrazinoacetic acid, dicyclohexylamine salt M.p. 179°–181°.

$C_{25}H_{37}Cl_2N_3O_3S$ Requires: C56.60, H7.03, N7.92, Cl 13.36, S6.04%. Found: C56.43, H6.99, N7.84, Cl 13.66, S6.08%.

(b)
(S)-2-[(2-Chlorophenyl)methylene]-1-(3-mercapto-2-methyl-1-oxopropyl)-1-hydrazinoacetic acid dicyclohexylamine salt M.p. 190°–191°.

$C_{25}H_{38}ClN_3O_3S$ Requires: C60.53, H7.72, N8.47, Cl 7.15, S6.46%. Found: C60.83, H7.79, N8.38, Cl 7.12, S6.47%.

(c)
(S)-1-(3-Mercapto-2-methyl-1-oxopropyl)-2[(3-pyridyl)methylene]-1-hydrazinoacetic acid M.p. 200°–201°.

$C_{12}H_{15}N_3O_3S$ Requires: C51.23, H5.37, N14.94, S11.40%. Found: C51.19, H5.37, N14.68, S11.38%.

(d)
(S)-1-(3-Mercapto-2-methyl-1-oxopropyl)-2[(2-pyridyl)methylene]-1-hydrazinoacetic acid M.p. 141°–143°.

$C_{12}H_{15}N_3O_3S$ Requires: C51.23, H5.37, N14.94, S11.40%. Found: C51.14, H5.42, N14.65, S11.51%.

(e)
(S)-1-(3-Mercapto-2-methyl-1-oxopropyl)-2[(2-thienyl)methylene]-1-hydrazinoacetic acid dicyclohexylamine salt M.p. 193°–195°.

$C_{11}H_{14}N_2O_3S_2.C_{12}H_{23}N$ Requires: C59.07, H7.97, N8.98, S13.71%. Found: C58.99, H7.82, N8.93, S13.63%.

(f)
(S)-1-(3-Mercapto-2-methyl-1-oxopropyl)-2-[(4-methoxy phenyl)methylene]-1-hydrazinoacetic acid M.p. 101°–3°.

$C_{14}H_{18}N_2O_4S$ Requires: C54.19, H5.81, N9.03, S10.32%. Found: C54.17, H5.77, N8.89, S10.47%.

(g)
(S)-1-(3-Mercapto-2-methyl-1-oxopropyl)-2-[(4-methyl-thiazol-2-yl)methylene)-1-hydrazinoacetic acid M.p. 138°–140°.

$C_{11}H_{15}N_3O_3S_2$ Requires: C43.85, H4.98, N13.95, S21.26%. Found: C43.50, H5.14, N13.77, S21.44%.

(h)
(S)-2-[(1,1'-biphenyl)-2-ylmethylene]-1-(3-mercapto-2-methyl-1-oxopropyl)-1-hydrazinoacetic acid dicyclohexylamine salt M.p. 154°–156°.

$C_{19}H_{20}N_2O_3S$ $C_{12}H_{23}N$ Requires: C69.27, H8.00, N7.82, S5.96%. Found: C68.83, H7.69, N7.61, S6.07%.

(i)
(S)-2-[(4-Butylphenyl)methylene]-1-(3-mercapto-2-methyl-1-oxopropyl)-1-hydrazinoacetic acid dicyclohexylamine salt M.p. 108°–110°.

$C_{17}H_{24}N_2O_3S$. $C_{12}H_{23}N$ Requires: C67.31, H9.09, N8.12, S6.19%. Found: C67.64, H9.21, N8.05, S6.25%.

(j)
(S)-2-[(2-Hydroxyphenyl)methylene]-1-(3-mercapto-2-methyl-1-oxopropyl)-1-hydrazinoacetic acid sodium salt Formed by treating an aqueous solution of the free acid with one equivalent of sodium bicarbonate, and freeze drying.

$C_{13}H_{15}N_2O_4S.Na$ 1.3$H_2O$. Requires: C45.66, H5.16, N8.20, S9.36%. Found: C45.60, H4.52, N7.90, S9.00%.

A mass spectrum (Fast Atom Bombardment) shows a peak at 319(M+Na+H)+.

(k)
(S)-N-(3-Mercapto-2-methyl-1-oxopropyl)-N-(1,2-dihydro-2-oxo-3-indolylimino)glycine M.p. 210°–212°.

$C_{14}H_{15}N_3O_4S$. Requires: C52.3, H4.67, N13.08, S9.97%. Found: C52.8, H5.08, N12.35, S9.67%.

EXAMPLE 5

1-[N-(1-(S)-Carboxy-3-phenylpropyl)-L-alanyl]-2-(phenylmethylene)-1-hydrazinoacetic acid hydrochloride

(a) t-Butyl 1-[N-(1-(S)-ethoxycarbonyl-3-phenylpropyl)-L-alanyl]-2-(phenylmethylene)-1-hydrazinoacetate A solution of t-butylhydrazinoacetate (1.45 g) in acetone (75 ml) was stirred at room temperature for 5 minutes. Dicyclohexylcarbodiimide (2.05 g) was added and the mixture stirred for a further 5 minutes. The hydrochloride salt of N-(1-S-ethoxycarbonyl-3-phenylpropyl)-S-alanine (3.15 g) was added to the foregoing mixture portionwise over 30 minutes and the resulting mixture stirred at room temperature for 20 h under nitrogen. The resulting solids were removed by filtration and the filtrate evaporated to an oil. A solution of the oil in 50% aqueous acetic acid was evaporated to dryness and the residue further dried by azeotropic distillation with toluene. A solution of the remaining gum in ethanol (100 ml) was treated with benzaldehyde (1.1 ml) and the solution heated at reflux for 3 hours. Triethylamine (1.54 ml) was added and the solution evaporated to a semi-solid. The residue was triturated with ether, the solids removed and the resulting filtrate evaporated to give the sub-title product as a light brown oil. The product was purified by chromatography on silica gel using ethyl acetate/petroleum ether as eluent. Yield=2.25 g.

Molecular weight of product=495.

Mass spectrum using fast atom bombardment showed an ion at 496 (i.e. M++1).

(b)

1-[N-(1-(S)-Ethoxycarbonyl-3-phenylpropyl)-L-alanyl]-2-(phenylmethylene)-1-hydrazinoacetic acid hydrochloride A solution of the product of step (a) (2.2 g) in trifluoroacetic acid (20 ml) was stirred at room temperature for 24 hours. The solution was evaporated to dryness and the residue re-evaporated with a mixture of toluene and dioxan (X3). A solution of the residual gum in dioxan was treated with ethereal HCl and the mixture again evaporated. The residual oil was triturated under ether to produce the sub-title product (1.8 g) as a white solid, mp—decomp from 170°.

$C_{24}H_{29}N_3O_5$.HCl Requires: C60.57, H6.31, N8.83, Cl7.47. Found: C60.11, H6.59, N8.72, Cl6.43.

(c)

1-[N-(1-(S)-Carboxy-3-phenylpropyl)-L-alanyl-2-(phenylmethylene)-1-hydrazinoacetic acid A solution of the product of step (b) (0.4g) in aqueous sodium hydroxide (0.165 g of NaOH in 4 ml water) was stirred at room temperature for 20 hours. The mixture was applied to a column of "Dowex" 50W-8X ("Dowex" is a Trade Mark) ion exchange resin (20 ml) and the resin was eluted with water to neutrality. The product was removed by elution with 2% aqueous pyridine. Product containing fractions were evaporated to dryness. The residue was triturated with ether and the title product (0.22 g) collected as the monohydrate by filtration.

M.p. 205°-7° (dec.).

$C_{22}H_{25}N_3O_5$. $H_2O$. Requires: C61.52, H6.34, N9.78%. Found: C61.40, H6.06, N10.32%.

The presence of 1.0 mole of water was confimed by Karl Fischer titration.

EXAMPLE 6

1-(N-(1-(S)-Carboxy-3-phenylpropyl)-L-alanyl]-2-(cyclohexylmethylene)-1-hydrazinoacetic acid (a) t-Butyl 2-(cyclohexylmethylene)-1-[N-(1-(S)-ethoxycarbonyl-3-phenylpropyl)-L-alanyl]-1-hydrazinoacetate The sub-title product was synthesised according to the method used for Example 5(a). The compound was isolated as a clear oil.

$C_{28}H_{43}N_3O_5$. Mw=501.

A mass spectrum showed (M+1)+ at 502 and a base peak at 234.

(b)

2-(Cyclohexylmethylene)-1-[N-(1-(S)-ethoxycarbonyl-3-phenylpropyl-L-alanyl]-1-hydrazinoacetic acid hydrochloride The sub-title product was synthesised according to the method used for Example 5(b).

M.p. 156°-8° (dec.).

$C_{24}H_{35}N_3O_5$ 1.15 HCl. Requires: C59.14, H7.48, N8.62, Cl 8.36%. Found: C58.90, H7.28, N8.51, Cl 8.36%.

(c)

1-[N-(1-(S)-Carboxy-3-phenylpropyl)-L-alanyl-2-(cyclohexylmethylene)-1-hydrazinoacetic acid The title product hydrate was synthesised according to the method used for Example 5(c).

M.p. 196°-8°.

$C_{22}H_{31}N_3O_5$. 1.1 $H_2O$. Requires: C60.50, H7.65, N9.62%. Found: C60.11, H7.48, N10.06%.

EXAMPLE 7

(S)-1-(3-Benzoylthio-2-methyl-1-oxopropyl)-2-cyclohexylmethylene-1-hydrozinoacetic acid sodium salt monohydrate (a) t-Butyl (S)-1-(3-benzoylthio-2-methyl-1-oxopropyl)-2-cyclohexylmethylene-1-hydrazinoacetate A mixture of t-butyl hydrazinoacetate oxalate (4.72 g), triethylamine (2.0 g) and cyclohexane carboxaldehyde (2.24 g) was stirred in ethanol (100 ml) for 16 hours at room temperature. The resulting solution was diluted with ether and the precipitate removed by filtration. The filtrate was evaporated to an oil and the residue re-evaporated with toluene to remove the last traces of ethanol. A solution of the oil in toluene (100 ml) was treated with polyvinylpyridine (7 g) and (S)-3-(benzoylthio)-2-methyl propanoyl chloride. The mixture was stirred under nitrogen for 16 hours. The reaction mixture was filtered and the filtrate stirred rapidly with saturated sodium bicarbonate solution for 1 hour. The organic layer was removed, washed with water and dried. Evaporation yielded an oil which was purified by flash chromatography on silica to give the sub-title product (8.5 g) as a gum.

(b)

(S)-1-(3-Benzoylthio-2-methyl-1-oxopropyl)-2-cyclohexylmethylene-1-hydrazinoacetic acid sodium salt monohydrate A solution of the product of step (a) (3.0 g) in trifluoroacetic acid (10 ml) was stirred at room temperature for 2 hours. The mixture was evaporated to an oil and the residue purified by flash chromatography to give the sub-title compound as the free acid (2.49 g) in the form of a gum.

A solution of the gum in methanol (30 ml) was treated with sodium bicarbonate solution (0.54 g in 20 ml of water). The methanol was removed by evaporation and the resulting aqueous solution freeze dried to give the title compound (2.5 g) as a white powder.

$C_{20}H_{25}N_2O_4SNa$. 1.25 $H_2O$ Requires: C55.22, H6.33, N6.45, S7.37%. Found: C55.42, H5.82, N6.32, S7.51%.

The presence of water was confirmed by Karl Fischer titration.

A mass spectrum (Fast Atom Bombardment) showed a major peak at 435 (M+Na)+.

EXAMPLE 8

2-[1-(3-Benzoylthio-1-oxopropyl)-2-(phenylmethylene)-1-hydrazino]-propanoic acid (a) t-Butyl 2-[1-(3-benzoylthio-1-oxopropyl)-2-(phenylmethylene)-1-hydrazino]-propanoate Prepared according to the method of Example 7(a). The compound was isolated as a clear oil.

$C_{24}H_{28}N_2O_4S$. Mw=440.

A mass spectrum showed M/e at 440(M+) with a base peak at 105.

(b)

2-[1-(3-Benzoylthio-1-oxopropyl)-2-(phenylmethylene)-1-hydrazino]-propanoic acid Prepared according to the method of Example 7(b). The product was isolated as the crystalline free acid. M.p. 149°–151°.

$C_{20}H_{20}N_2O_4S$ Requires: C62.50, H5.21, N7.29, S8.33%. Found: C62.31, H5.40, N7.59, S8.58%.

EXAMPLE A

In vitro Assay of inhibitors of Angiotensin Converting Enzyme

The method is based upon that of Cushman and Cheung (1971) but uses a radioactive substrate [glycine-1-$^{14}$C] hippuryl-L-histidyl-L-leucine (HHL) whose hydrolysis may be determined by liquid scintillation counting of released [$^{14}$C]-hippuric acid. Hydrolysis of 2 mM HHL by an extract of rabbit lung acetone powder (Sigma) over a 30 min incubation period at 37° is followed by acidification of the reaction mixture and extraction of [$^{14}$C]hippurate with ethyl acetate.

Potential inhibitors are tested initially at 0.01 mM and if found active are retested at lower concentrations to determine an IC$_{50}$. Dimethyl sulphoxide at 1% final concentration may be used as a solubility aid without affecting enzyme activity. Compounds of special interest are studied at a range of substrate and inhibitor concentrations to determine the type of inhibition and are also tested against other enzymes, e.g. carboxypeptidase A to establish their specificity for ACE.

EXAMPLE B

Antihypertensive effects were investigated in conscious spontaneously hypertensive rats (SHR) of the Okamoto strain. Systolic blood pressure and heart rate were measured by the tail cuff method using an electrosphygmomanometer 1 hour before and 1, 3, 5 and 24 hours after oral dosing with the compound (dose range 0.1–100 mg/kg p.o.). Percentage changes in each parameter were measured with respect to pretreatment control values.

We claim:

1. A compound of formula I,

ZCHRCON(—N=CR$_4$R$_5$)CHR$_6$(CH$_2$)$_n$COY in which
Z is R$_2$CH(COOH)NH—, R$_1$SCH$_2$— or Ph(CH$_2$)$_p$PO(OH)—,
Ph is phenyl,
p is an integer from 1 to 6,
R$_1$ is hydrogen or R$_8$CO—,
R$_8$ is alkyl C1 to 10 or phenyl,
R is hydrogen or alkyl C1 to 10,
R$_2$ is alkyl C1 to 10 or phenylalkyl C7 to 12,
R$_4$ and R$_5$, which may be the same or different, are each hydrogen, phenyl, naphthyl; a heterocyclic group selected from thiophenyl, furyl, pyrrolyl, imidazol, oxazolyl, thiazolyl, pyrimidinyl and pyridyl, each of which is optionally fused to a benzene ring; a 5 or 6 membered alicyclic ring fused to a benzene ring; cycloalkyl containing 3 to 7 carbon atoms, or alkyl C1 to 10 optionally substituted by phenyl, naphthyl or a heterocyclic group selected from thiophenyl, furyl, pyrrolyl, imidazolyl, oxazolyl, thiazolyl, pyrimidinyl and pyridyl, each of which is optionally fused to a benzene ring, when R$_4$ or R$_5$ are phenyl, naphthyl, a 5 or 6 membered alicyclic ring or a heterocyclic group as defined above, said phenyl, naphthyl, alicyclic ring or heterocyclic group can be optionally substituted by one or more alkyl C1 to 10 alkoxy C1 to 10, halogen, phenylalkyl C7 to 12, phenylalkoxy C7 to 12, phenyl, hydroxy, =O, fluoroalkyl C1 to 10, cyano, nitro, phenylsulphonamido, dialkyl (C1 to 10)-amino-alkoxy (C1 to 10), alkylthio C1 to 10, or dialkyl (C1 to 10)-amino, or R$_4$ and R$_5$ together form a —(CH$_2$)$_4$—, —(CH$_2$)$_5$—,

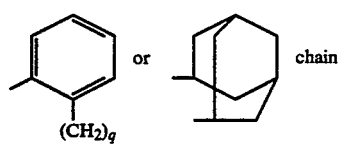

R$_6$ is hydrogen or alkyl C1 to 10,
q is 2 or 3,
n is 0 or 1,
Y is hydroxy or —NHSO$_2$R$_9$, and
R$_9$ is alkyl C1 to 10,
and pharaceutically acceptable salts, alkyl C1 to 6 and benzyl esters thereof.

2. A compound according to claim 1, wherein Z is R$_2$CH(COOH)NH— or R$_1$SCH$_2$—, n is O and Y is —OH.

3. A compound according to claim 2, wherein R is hydrogen or methyl and R$_6$ is hydrogen or methyl.

4. A compound according to claim 3, wherein R$_2$ is benzyl or phenylethyl or R$_1$ is hydrogen, benzoyl, acetyl or pivaloyl.

5. A compound according to claim 1, wherein one of R$_4$ and R$_5$ is hydrogen, methyl or phenyl and the other is naphthyl, cyclohexyl, alkyl C1 to 4, pyridyl, thienyl, thiazolyl which may be substituted alkyl C1 to 6; or phenyl optionally substituted by one or two chlorine atoms, by —CN, by phenylsulphonylamino, by another phenyl, by alkoxy C1 to 6, by alkyl C1 to 6 or by hydroxy; or wherein R$_4$ and R$_5$ together form a dihydronaphthylidene, a cyclohexylidene, an adamantylidene or an optionally oxo substituted dihydroindolyl group.

6. A compound according to claim 1 in which R$_2$ is phenylethyl, R is methyl, R$_4$ and R$_6$ are both hydrogen, R$_5$ is phenyl, or alkyl or cylindrical containing up to 6 carbon atoms, n is O and Y is —OH.

7. A compound according to claim 1 in which R$_1$ is hydrogen or R$_8$ is phenyl, R is methyl, R$_4$ is hydrogen, R$_5$ is alkyl or cycloalkyl containing up to 6 carbon atoms, n is O and Y is —OH.

8. A compound of formula Ia,

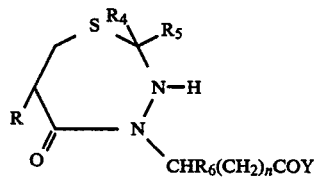

in which R, $R_4$, $R_5$, $R_6$, n and Y are as defined in claim 1.

9. A compound selected from
(S)-1-(3-Mercapto-2-methyl-1-oxopropyl)-2-(phenylmethylene)-1-hydrazinoacetic acid,
Ethyl(S)-1-(3-acetylthio-2-methyl-1-oxopropyl)-2-(phenylmethylene)hydrazinoacetate,
(S)-1-(3-Mercapto-2-methyl-1-oxopropyl)-2-(1-naphthylmethylene)-1-hydrazinoacetic acid,
(S)-1-(3-Mercapto-2-methyl-1-oxopropyl)-2-(2-naphthylmethylene)-1-hydrazinoacetic acid,
(S)-1-(3-Mercapto-2-methyl-1-oxopropyl)-2-(3,4-dihydronaphthylidene)-1-hydrazinoacetic acid,
2-[(2,6-Dichlorophenyl)methylene]-1-(3-mercapto-1-oxopropyl)-1-hydrazinoacetic acid,
(S)-1-(3-Mercapto-2-methyl-1-oxopropyl)-2-(1-phenylethylidene)-1-hydrazinoacetic acid,
(S)-1-(3-Mercapto-2-methyl-1-oxopropyl)-2-(diphenylmethylidine)-1-hydrazinoacetic acid,
(S)-2-[(4-Cyanophenyl)methylene]-1-(3-mercapto-2-methyl-1-oxopropyl)-1-hydrazinoacetic acid,
(S)-2-[((4-Phenylsulphonamido)phenyl)methylene]-1-(3-mercapto-2-methyl-1-oxopropyl)-1-hydrazinoacetic acid,
(S)-2-Cyclohexylmethylene-1-(3-mercapto-2-methyl-1-oxopropyl)-1-hydrazinoacetic acid,
2-Cyclohexyl-hexahydro-6-(S)-methyl-5-oxo-[1,3,4-thiadiazepinyl]-4-acetic acid,
(S)-1-(3-Mercapto-2-methyl-1-oxopropyl)-2-(2-methyl propylidene)-1-hydrazinoacetic acid,
Hexahydro-6-methyl-2-(1-methyl-ethyl)-5-oxo-[1,3,4-thiadiazepinyl]-4-acetic acid,
(S)-2-Adamantylidene-1-(3-mercapto-2-methyl-1-oxopropyl)1-hydrazinoacetic acid,
Hexahydro-6-(S)-methyl-5-oxo-spiro[1,3,4-thiadiazepine-2,2'-tricyclo-[3,3,1,1$^{3,7}$]decane]-4-acetic acid,
(S)-2-Adamantylidene-1-(3-mercapto-2-methyl-1-oxopropyl)-1-hydrazinoacetic acid,
Hexahydro-6-(S)-methyl-5-oxo-spiro[1,3,4-thiadiazepine-2,2'-tricyclo-[3,3,1,1$^{3,7}$]decane]-4-acetic acid,
(S)-2-[(1,1'-Biphenyl)-4-ylmethylene]-1-(3-mercapto-2-methyl-1-oxopropyl)-1-hydrazinoacetic acid,
(S)-2-Cyclohexylidene-1-(3-mercapto-2-methyl-1-oxopropyl)-1-hydrazinoacetic acid,
(S)-1-(3-Mercapto-2-methyl-1-oxopropyl)-2-(2,2-dimethylpropylidene)-1-hydroazinoacetic acid,
(S)-2-(4-Chlorophenylmethylene)-1-(3-mercapto-2-methyl-1-oxopropyl)-1-hydrazinoacetic acid,
Ethyl (S)-1-(3-acetylthio-2-methyl-1-oxopropyl)-2-(4-chlorophenylmethylene)-1-hydrazinoacetate,
(S)-2-[(2,6-Dichlorophenyl)methylene]-1-(3-mercapto-2-methyl-1-oxopropyl)-1-hydrazinoacetic acid,
(S)-2-[(2-Chlorophenyl)methylene]-1-(3-mercapto-2-methyl-1-oxopropyl)-1-hydrazinoacetic acid,
(S)-1-(3-Mercapto-2-methyl-1-oxopropyl)-2[(3-pyridyl)methylene]-1-hydrazinoacetic acid,
(S)-1-(3-Mercapto-2-methyl-1-oxopropyl)-2[(2-pyridyl)methylene]-1-hydrazinoacetic acid,
(S)-1-(3-Mercapto-2-methyl-1-oxopropyl)-2[(2-thienyl)methylene]-1-hydrazinoacetic acid,
(S)-1-(3-Mercapto-2-methyl-1-oxopropyl)-2-[(4-methoxyphenyl)methylene]-1-hydrazinoacetic acid,
(S)-1-(3-Mercapto-2-methyl-1-oxopropyl)-2-[(4-methylthiazol-2-yl)methylene]-1-hydrazinoacetic acid,
(S)-2-[(1,1'-biphenyl)-2-ylmethylene]-1-(3-mercapto-2-methyl-1-oxopropyl)-1-hydrazinoacetic acid,
(S)-2-[(4-Butylphenyl)methylene]-1-(3-mercapto-2-methyl-1-oxopropyl-1-hydrazinoacetic acid,
(S)-2-[(2-Hydroxyphenyl)methylene]-1-(3-mercapto-2-methyl-1-oxopropyl)-1-hydrazinoacetic acid,
(S)-N-(3-Mercapto-2-methyl-1-oxopropyl)-N-(1,2-dihydro-2-oxo-3-indolylimino)glycine,
1-[N-(1-(S)-Carboxy-3-phenylpropyl)-L-alanyl]-2-(phenylmethylene)-1-hydrazinoacetic acid,
t-Butyl 1-[N-(1-(S)-ethoxycarbonyl-3-phenylpropyl)-L-alanyl]-2-(phenylmethylene)-1-hydrazinoacetate,
1-[N-(1-(S)-Ethoxycarbonyl-3-phenylpropyl)-L-alanyl]-2-(phenylmethylene)-1-hydrazinoacetic acid,
1-(N-(1-(S)-Carboxy-3-phenylpropyl)-L-alanyl]-2-(cyclohexylmethylene)-1-hydrazinoacetic acid,
t-Butyl 2-(cyclohexylmethylene)-1-[N-(1-(S)-ethoxycarbonyl-3-phenylpropyl)-L-alanyl]-1-hydrazinoacetate,
2-(Cyclohexylmethylene)-1-[N-(1-(S)-ethoxycarbonyl-3-phenylpropyl)-L-alanyl]-1-hydrazinoacetic acid,
(S)-1-(3-Benzoylthio-2-methyl-1-oxopropyl)-2-cyclohexylmethylene-1-hydrazinoacetic acid,
t-Butyl (S)-1-(3-benzoylthio-2-methyl-1-oxopropyl)-2-cyclohexylmethylene-1-hydrazinoacetate,
2-[1-(3-Benzoylthio-1-oxopropyl)-2-(phenylmethylene)-1-hydrazino]propanoic acid,
t-Butyl 2-[1-(3-benzoylthio-1-oxopropyl)-2-(phenylmethylene)-1-hydrazino]-propanoate,
and pharmaceutically acceptable salts of any one thereof.

10. A pharmaceutical composition comprising an antihypertensive amount of a compound according to claim 1 in admixture with a pharmaceutically acceptable adjuvant, diluent or carrier.

11. A method of treatment of hypertension, which comprises administering an effective amount of a compound according to claim 1 to a patient suffering from hypertension.

* * * * *